United States Patent
Kikuchi et al.

(10) Patent No.: US 8,980,625 B2
(45) Date of Patent: Mar. 17, 2015

(54) CELL CULTURE PLATE AND METHOD OF MANUFACTURING THE SAME

(75) Inventors: Yuji Kikuchi, Tokyo (JP); Hiroko Kikuchi, Sapporo (JP); Taiji Nishi, Tokyo (JP); Takenori Kitani, Tsukuba (JP); Yukihiro Yanagawa, Kamisu (JP); Motohiro Fukuda, Tsukuba (JP)

(73) Assignees: National Food Research Institute, Tsukuba-shi (JP); Kuraray Co., Ltd., Kurashiki-shi (JP)

( * ) Notice: Subject to any disclaimer, the term of this patent is extended or adjusted under 35 U.S.C. 154(b) by 1060 days.

(21) Appl. No.: 11/360,535

(22) Filed: Feb. 24, 2006

(65) Prior Publication Data
US 2007/0202589 A1  Aug. 30, 2007

(51) Int. Cl.
| | |
|---|---|
| C12M 1/22 | (2006.01) |
| C12M 3/00 | (2006.01) |
| C12M 1/12 | (2006.01) |
| C12M 1/00 | (2006.01) |
| C12M 3/06 | (2006.01) |
| B01L 3/00 | (2006.01) |

(52) U.S. Cl.
CPC .............. C12M 23/16 (2013.01); B01L 3/5027 (2013.01)
USPC .................. 435/305.1; 435/283.1; 435/289.1; 435/297.5; 435/305.2

(58) Field of Classification Search
USPC ........................................... 435/283.1–309.4
See application file for complete search history.

(56) References Cited

U.S. PATENT DOCUMENTS

| | | | | |
|---|---|---|---|---|
| 5,656,414 A | * | 8/1997 | Chou et al. ..................... | 430/312 |
| 5,792,653 A | * | 8/1998 | Weibezahn et al. ......... | 435/288.5 |
| 6,541,187 B1 | * | 4/2003 | Wang et al. ..................... | 430/324 |
| 6,548,263 B1 | * | 4/2003 | Kapur et al. ..................... | 506/32 |
| 6,764,688 B2 | * | 7/2004 | Yamashita et al. .......... | 424/278.1 |
| 2003/0219752 A1 | * | 11/2003 | Short ................................. | 435/6 |
| 2004/0067585 A1 | * | 4/2004 | Wang et al. ..................... | 435/395 |
| 2004/0144484 A1 | * | 7/2004 | Fisher ........................... | 156/292 |
| 2004/0191704 A1 | | 9/2004 | Nishi et al. | |
| 2004/0224380 A1 | * | 11/2004 | Chou et al. ....................... | 435/29 |
| 2004/0245669 A1 | | 12/2004 | Nishi et al. | |
| 2005/0032204 A1 | * | 2/2005 | Rodgers et al. ............. | 435/288.5 |
| 2005/0167370 A1 | * | 8/2005 | Nakajima et al. ............. | 210/767 |
| 2006/0154361 A1 | * | 7/2006 | Wikswo et al. ............ | 435/289.1 |

FOREIGN PATENT DOCUMENTS

| | | |
|---|---|---|
| JP | 11-169166 | 6/1999 |
| JP | 2002-153260 | 5/2002 |

(Continued)

OTHER PUBLICATIONS

H. Kaji et al., Development of Novel Bioassay System Using Micropatterned Cardiac Myocytes (partial English translations).
Hiroyuki Moriguchi et al., "On-chip Neural Cell Cultivation using Agarose-microchamber Array constructed by Photo-thermal Etching Method" (partial English translations).
Kazunori Okano et al., "Separation and preparation of cells and biological molecules" (partial English translations).
U.S. Appl. No. 12/665,474, filed Dec. 18, 2009, Tazaki, et al.
U.S. Appl. No. 13/229,087, filed Sep. 9, 2011, Tazaki, et al.

(Continued)

Primary Examiner — Nathan Bowers
Assistant Examiner — Lydia Edwards
(74) Attorney, Agent, or Firm — Oblon, McClelland, Maier & Neustadt, L.L.P.

(57) ABSTRACT

A cell culture plate has a plurality of flow channels, uneven pattern areas and through holes. The flow channels are formed between the uneven pattern areas, and culture solution flows from the flow channels into the uneven pattern areas or from the uneven pattern areas into the flow channels. The uneven pattern area has uneven patterns that create a cell culture space.

17 Claims, 7 Drawing Sheets

(56) References Cited

FOREIGN PATENT DOCUMENTS

| JP | 2004-148519 | 5/2004 |
|---|---|---|
| JP | 2004-148693 | 5/2004 |
| JP | 2004-195730 | 7/2004 |
| JP | 2004-284225 | 10/2004 |
| JP | 2005-265634 | 9/2005 |
| WO | WO 03/028970 | 4/2003 |
| WO | WO 03/028970 A1 | 4/2003 |

OTHER PUBLICATIONS

H. Kaji et al., Development of Novel Bioassay System Using Micropatterned Cardiac Myocytes (partial English translations), Nov. 2002.

Hiroyuki Moriguchi et al., "On-chip Neural Cell Cultivation using Agarose-microchamber Array constructed by Photothermal Etching Method" (partial English translations), Nov. 2002.

Kazunori Okano et al., "Separation and preparation of cells and biological molecules" (partial English translations), Dec. 2001.

* cited by examiner

Fig. 1

Fig. 3A
[TOP VIEW]

[UNIT : μm]

| NUMBER OF BLOCKS | 3 BY 60 |
|---|---|
| NUMBER OF BLOCKS | 1000 (μm) |
| NUMBER OF BLOCKS | 200 × 60=12001 (μm) |

Fig. 3B
[SIDE VIEW]

Fig. 4A [TOP VIEW]

Fig. 4B [SIDE VIEW]

Fig. 5A
[TOP VIEW]

Fig. 5B
[SIDE VIEW]

Fig. 6A
[TOP VIEW]

[UNIT : μm]

Fig. 6B
[SIDE VIEW]

Fig. 7

CELL CULTURE PLATE AND METHOD OF MANUFACTURING THE SAME

BACKGROUND OF THE INVENTION

1. Field of the Invention

The present invention relates to a cell culture plate suitable for use in bioassay to evaluate the effects of drugs or to test the toxicity of drugs with the use of cultured cells and a method of manufacturing the cell culture plate.

2. Description of Related Art

A technique of using cells isolated from tissue for tests and inspections is essential in biotechnological fields. This technique is widely applied to diagnosis on disease and pathology, search for new drugs and determination of drug efficacy, animal inspection, plant inspection, environmental pollutant test and so on. Though isolated cells are sometimes used immediately for test, in many cases they are cultured in a culture dish or a test tube by a cell culture method. Various inspections are conducted in a culture system.

The assay normally sets uniform culture systems and checks the efficacy of drugs to be evaluated with varied amount and concentration. It thus uses cell culture vessels that are formed uniformly. The culture vessel is typically a culture dish. 6-well, 12-well, 48-well and 96-well plates are generally used as culture dishes. Further, due to the recent trend of use of minute amounts, a 384-well plate having a number of culture dishes with small bores has been used lately.

However, use of a commercially available cell culture dish for culturing tissue cells causes the cells to be thinned into a form in lack of direction and to cease to express the features observed in vivo. This is because the culturing on a well plate, which is vessel shaped, is substantially the same as the culturing on a flat plate for a cell with the size of several μm to several tens of μm. Particularly, in the growth of tissue cells that are difficult to culture, such as hepatic cells, it is further difficult to maintain the features they have in vivo.

An approach to overcome the above drawback is to form a minute uneven pattern suitable for the growth of tissue cells on a culture plate and culture the cells on the plate. This approach aims at arranging the cells on the minute uneven pattern and growing them sterically with direction. This technique, however, fails to bring out the features observed in vivo by the growth of the cells due to lack of keeping the freshness of culture solution.

A normal cell culture process soaks a culture plate in culture solution for one to several days. As a human body receives oxygen and nutrients through blood in vivo and expels waste products, a cell receives oxygen and nutrients from culture solution and expels waste products into the culture solution. The waste products affect the growth of the cell, and thus the culture solution is replaced a plurality of times when conducting the cell growth for several days, which causes the solution freshness to vary, thus failing to maintain the features observed in vivo.

In order to preserve the same culture environment while varying the culture conditions in one culture plate, a technique of changing culture areas is proposed, for example, in Japanese Unexamined Patent Publication No. 11-169166. The technique uses a culture vessel in which culture dishes whose cell culture areas vary at given rate are arranged in succession. The culture dishes, for example, have the culture areas that vary successively like 100%, 75%, 50%, 25% and 0%. It is thereby possible to control the number of culture cells without changing the culture environment, which enables the use of the culture plate for bioassay in various conditions.

As described above, the use of a conventional cell culture dish causes cells to be thinned to cease to present the features they have in vivo. On the other hand, culturing cells on a minute uneven pattern in order to grow the cells sterically with direction decreases the freshness of culture solution due to waste products discharged into the culture solution, and the cells thereby do not present the features they have in vivo.

SUMMARY OF THE INVENTION

As a result of investigations to solve the above problems, the inventors of the present invention have found that a plate having an uneven pattern that forms a spatial structure for cell culturing is a cell culture plate suitable for bioassay or the like and accomplished the present invention.

According to an aspect of the present invention, there is provided a cell culture plate for culturing cells, which includes an uneven pattern creating a spatial structure in which cells are arranged and cultured. It is thereby possible to solve the problem that cells are thinned to cease to express the features in vivo when cultured in a large space. Preferably, the cell culture plate further have a flow channel though which culture solution and/or reagent flow. Preferably, the cell culture plate may further have a mixing portion where culture solution and/or reagent are mixed. Alternatively, it is preferred for the cell culture plate to have an electrode for electrical cell fusion. It is thereby possible to provide a cell culture plate in accordance with applications.

Preferably, the width of the flow channel of the cell culture plate may be from 1 μm to 1000 μm and a depth of the flow channel is from 1 μm to 1000 μm, preferably, in terms of culture solution supply and integration. Alternatively, the height of the spatial structure which is created by the uneven pattern of the cell culture plate and in which cells are arranged and cultured may be from 3 μm to 1000 μm, a width is from 3 μm to 1000 μm and a depth is from 3 μm to 1000 μm, preferably. Also preferably, the uneven pattern of the cell culture plate may include an uneven pattern with a height of from 20 nm to 100 μm and a width or pitch of from 20 nm to 100 μm.

It is preferred that the cell culture plate is provided with surface treatment for cell immobilization. It is also preferred that the cell culture plate is a lamination of a plurality of plates. It is thereby possible to efficient cell growth. Alternatively, it is preferable that the cell culture plate may further have a second flow channel, and the flow channel and the second flow channel may be connected to the uneven pattern, culture solution and/or reagent may flow from the flow channel into the uneven pattern, and culture solution and/or reagent may flow from the uneven pattern into the second flow channel. It is thereby possible to perform the supply of culture solution and/or reagent and the discharge of by-products and so on effectively.

According to another aspect of the present invention, there is provided a method of manufacturing a cell culture plate having an uneven pattern creating a spatial structure in which cells are arranged and cultured, which includes forming a resist pattern on a substrate, forming a metal structure having a reverse pattern of a structure pattern of the cell culture plate by depositing a metal in accordance with the resist pattern formed on the substrate or a transcription pattern thereof, and forming a resin molded cell culture plate by transcribing the pattern of the cell culture plate. It is thereby possible to manufacture a desired cell culture plate effectively.

In this method, the step of forming the resist pattern on the substrate may include a step of repeating formation and exposure of resist layer a plurality of times until the resist layer is formed into a structural body having a predetermined height or depth. This enables to manufacture a cell culture plate having a desired height or depth. Further, it is preferred in this method that the step of forming the resist pattern on the substrate further includes mask positioning for positioning mask patterns so that positions of mask patterns of a plurality of layers are aligned upon exposure when repeating formation and exposure of the resist layer a plurality of times. This enables to manufacture a cell culture plate with high accuracy. It is also preferred in this method that the step of forming the resist pattern on the substrate uses different resists having different sensitivities for each resist layer when repeating formation and exposure of the resist layer a plurality of times. This enables to produce a resist pattern with further accuracy.

The present invention provides a cell culture plate that allows effective cell culture and a method of manufacturing the cell culture plate.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE PREFERRED EMBODIMENTS

The preferred embodiments of the present invention will be described hereinbelow. The explanation provided hereinbelow merely illustrates the embodiments of the present invention, and the present invention is not limited to the below-described embodiments. The description hereinbelow is appropriately shortened and simplified to clarify the explanation. A person skilled in the art will be able to easily change, add, or modify various elements of the below-described embodiments, without departing from the scope of the present invention.

Figure 1:
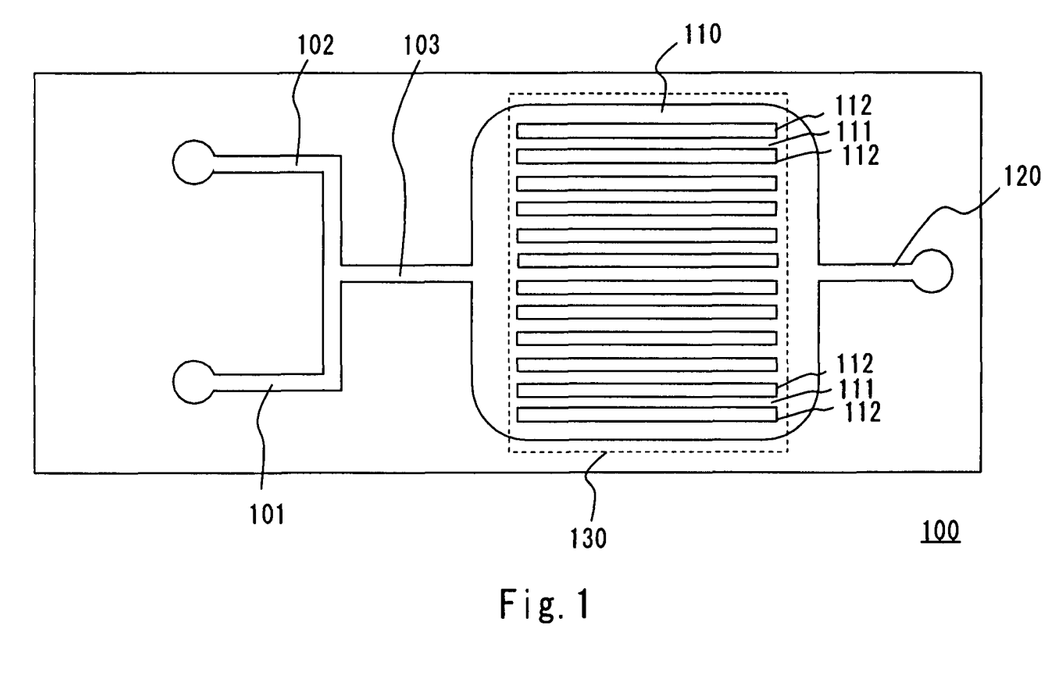
FIG. 1 is a structural view showing an example of a cell culture plate according the present invention.

The present invention is described hereinafter in detail. A cell culture plate of this invention has a flow channel through which culture solution flows and an uneven pattern on which cells are cultured. FIG. 1 shows an example of the structure of a cell culture plate 100 according to the present invention. The cell culture plate 100 has a mixing portion 103 where two flow channels 101 and 102 converge. Fluid such as culture solution and reagent that are mixed in the mixing portion 103 then flows into a culture area 110. In the culture area, a plurality of flow channels 111 through which the fluid flows and an uneven pattern area 112 that has uneven patterns forming a spatial structure for cell culture and serves as a culture medium are formed. In the culture medium, a flow channel for culture solution is formed by the uneven patterns. By-products of the cells are discharged from the culture area 110 through the flow channel 120. The cell culture plate 100 further has an electrode 130 for electrical cell fusion.

The flow channel through which culture solution flows is described below. The flow channel constantly supplies cells with fresh culture solution so as to prevent decrease in freshness of culture solution due to waste products expelled from cells and thereby prevent the cells from ceasing to exert the features they have in vivo. The flow channel may have any shape as long as it can supply culture solution. Though reduction in width and depth of the flow channel makes a high-density cell culture plate, it is preferred to set appropriate width and depth so as to secure a sufficient supply amount of culture solution. The width and depth of the flow channel are preferably within the range of from 1 µm to 1000 µm and more preferably from 3 µm to 500 µm in order to enable the supply of culture solution while achieving an efficient integrated cell culture plate.

The flow channel for supplying culture solution may be also used as a flow channel for supplying reagent or the like. It is also feasible to form a flow channel for culture solution and a flow channel for reagent or the like separately. For example, culture solution may flow through the flow channel 101 and reagent or the like may flow through the flow channel 102 in FIG. 1. The flow channel for supplying culture solution or reagent or the like may directly supply the fluid to the uneven pattern for culturing cells. Alternatively, a cell culture plate may have a mixing portion where the flow channel for culture solution and the flow channel for reagent or the like converge to mix the culture solution and the reagent or the like, such as the mixing portion 103 in FIG. 1. The mixture made in the mixing portion is then supplied to the uneven pattern directly or through the flow channel. By supplying the culture solution and the reagent or the like to the uneven pattern for culturing cells, by-products are produced from the cells. The cell culture plate may have a flow channel for retrieving these products, such as the flow channel 120 in FIG. 1.

The cell culture plate may have the flow channel 111 and the uneven pattern area 112 serving as a culture medium that has a plurality of flow channels for supplying culture solution and has an uneven pattern for culturing cells between the flow channels as shown in FIG. 1. The culture solution supplied from the flow channel 111 flows through a supply port into the uneven pattern 112. Alternatively, the cell culture plate may have a structure where culture solution flows on a culture medium having uneven patterns for culturing cells. In this structure, the width of a flow channel may be the same as the width of the cell culture plate at most. Performing surface treatment for immobilize cells on the cell culture plate prevents the cells from flowing out of the culture medium. In addition, it is also feasible to form a tubular flow channel by superposing a glass or plastic plate onto the culture plate.

The uneven pattern for culturing cells is described below. The uneven pattern for culturing cells avoids that the cells are thinned into a form in lack of direction and cease to present the features observed in vivo and enables to culture the cells sterically. A minute uneven pattern is formed on the surface of a substrate so that cells grow in a spatial structure. The spatial structure for growing the cells may be made by superposing a glass or a plastic plate. The uneven pattern may have any shape as long as it is suitable for the purpose of culturing cells. It is preferred to select the shape of the uneven pattern appropriately in terms of industrial technologies and manufacturing costs. The height, width or depth of the uneven pattern are preferably within the range of from 3 µm to 1000 µm and more preferably from 5 µm to 500 µm in order to culture the cells sterically.

The spatial structure for culturing cells may have a minute uneven pattern of 20 nm to 100 µm or more preferably 50 nm to 50 µm at its bottom, for example, in order to enhance the growth of cells. The height, width or pitch of the minute uneven pattern is preferably 1 µm to 100 µm and more preferably 3 µm to 50 µm in terms of industrial reproducibility. Further, if a more minute uneven pattern is formed by silicon dry etching, for example, it is expected to separate and extract substances or the like generated from cells by the size in molecular level, for example. The height, width or pitch of the minute uneven pattern in this case is preferably 20 nm to 3 µm and more preferably 50 nm to 1 µm for efficient separation and extraction. The size of the uneven pattern or the minute uneven pattern may be based on the maximum size.

Though a preferred material of the culture plate is plastic for its high efficiency in surface treatment, any material, including glass and silicon, may be used as long as it is not be toxic for cultured cells and it can be surface-treated. Further, the use of transparent material that allows transmitted light observation is preferred when observing the growth process of cells by using a fluorescence microscope, for example.

A method of manufacturing a cell culture plate according to the present invention is not particularly limited as long as it can produce a plate of a desired shape. Generally, a method such as dry etching and wet etching on silicon or glass material is used, for example. As a molding method of resin material, extrusion, injection, hot embossing, nanoimprinting, blowing, calendaring, casting, press molding and so on may be used.

A cell culture plate of the present invention may have an electrode for electrical cell fusion. A purpose of electrical cell fusion is to obtain two different kinds of cells by the electrical cell fusion and acquire by-products. One method for forming an electrode is to perform masking on a cell culture plate and deposit a conductive film such as gold, silver, platinum, copper, aluminum, ITO by vapor deposition, sputtering and so on.

Laminating the cell culture plates of the present invention allows conducting a plurality of cell culturing at the same time, thus enabling to provide a culture plate suitable for bioassay efficiently. When using the cell culture plate of this invention in lamination, it is necessary to align through holes and so on for supplying culture solution. The alignment may be made by techniques such as marking on corresponding positions of cell culture plates and positioning with a light microscope, CCD camera and so on or positioning with a laser interferometer.

It is possible to provide a prescribed surface treatment on the culture plate of the present invention. Various methods may be used for the surface treatment to enhance the adhesion of cells, including methods of using low-temperature plasma, corona discharge, ultraviolet irradiation and so on and a method of applying collagen or the like that is a protein to enhance the cell adhesion. It is also feasible to coat a certain part to modify an arbitrary part.

A method of manufacturing a cell culture plate according to an embodiment of the present invention is described hereinafter with reference to FIGS. 2A to 2E. The manufacturing method of this embodiment forms a metal structure by depositing a metal in accordance with a resist pattern formed on a substrate and then forms a resin molded product by using the metal structure. The cell culture plate produced by the manufacturing method of this embodiment has high accuracy in spite of being a resin molded product. Further, the manufacturing method of a cell culture plate allows producing a highly accurate cell culture plate at low costs, and therefore it is particularly effective for mass-use industrial applications in which the advantage of low costs is especially valuable.

The method of manufacturing a cell culture plate according to this embodiment firstly forms a desired resist pattern. Then, it deposits a metal structure on a substrate by plating in accordance with the resist pattern. The method then forms a resin molded product by using the metal structure as a mold, thereby producing a cell culture plate.

The process of forming the resist pattern is described in further detail below with reference to FIGS. 2A to 2E. The resist pattern formation process of this embodiment includes:
  (i) formation of a first resist layer on a substrate;
  (ii) positioning of the substrate and a first mask;
  (iii) exposure of the first resist layer with the use of the first mask;
  (iv) heat treatment on the first resist layer;
  (v) formation of a second resist layer on the first resist layer;
  (vi) positioning of the substrate and a second mask;
  (vii) exposure of the second resist layer with the use of the second mask;
  (viii) heat treatment on the second resist layer; and
  (ix) development of the resist layers.

When forming a structure having different levels of a depth of 30 µm and a depth of 100 µm, for example, on a substrate, a first resist layer with a thickness of 70 µm and a second resist layer with a thickness of 30 µm are successively deposited on the substrate, and an exposure process or exposure and heat treatment processes are performed upon deposition of each layer. By a following development process, a pattern with a depth of 30 µm, which is the second resist layer, is obtained firstly and then a pattern with a depth of 100 µm, which is a combination of the first resist layer and the second resist layer, is obtained. In order to prevent the pattern with a depth of 30 µm as the second resist layer from dissolving into developer or being deformed at the time when the pattern with a depth of 100 µm is obtained, it is required to control the solubility of each layer into developer.

In the case of forming a resist layer by spin coating, it is possible to express alkali resistance by adjusting a baking (solvent drying) time of the second resist layer. One technique for expressing the alkali resistance of photodegradable positive resist is to increase a baking time (solvent drying time) so as to harden the resist. The baking time of the resist is normally adjusted according to the thickness of a layer, the density of solvent such as thinner, and the sensitivity. Increasing the baking time can express the alkali resistance. Overbaking of the first resist layer hardens the resist too much, making it difficult to dissolve a light-exposed part and form a pattern in the subsequent development step. Thus, it is preferred to adjust baking conditions by reducing the baking time and so on. Equipment used for the baking is not particularly limited as long as it can dry a solvent, including an oven, a hot plate, a hot-air dryer, and so on. Since the expression of the alkali resistance is limited compared to photocrosslinkable negative resist, the combined thickness of the resist layer is preferably 5 to 200 µm and more preferably 10 to 100 µm.

Besides the optimization of the baking time, another method for expressing the alkali resistance of the photocrosslinkable negative resist is optimization of crosslink density. Normally, the crosslink density of the negative resist may be adjusted by the exposure amount. In the case of chemical amplification resist, it may be adjusted by the exposure amount and the heat-treatment time. The alkali resistance can be expressed by increasing the exposure amount or the heat-treatment time. When using the photocrosslinkable negative resist, the combined thickness of the resist layer is preferably 5 to 500 µm, and more preferably, 10 to 300 µm.

The manufacturing method according to this embodiment is described hereinafter in detail with reference to FIGS. 2A to 2H.

Figures 2A, 2B:
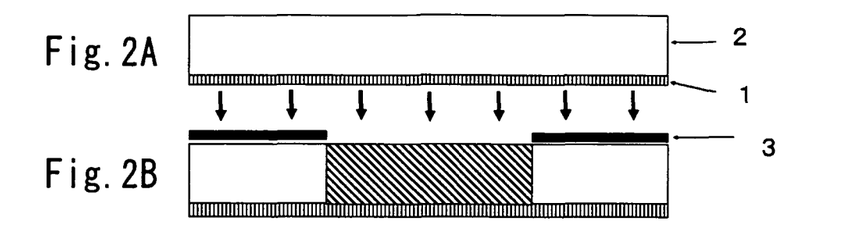
FIGS. 2A to 2H are schematic views showing the steps of manufacturing a cell culture plate according to an embodiment of the present invention.

(i) The formation of the first resist layer 2 on the substrate 1, which is shown in FIG. 2A, is described below. The flatness of a cell culture plate to be obtained by a molded product formation step is determined by the step of forming the first resist layer on the substrate. Thus, the flatness when the first resist layer 2 is deposited on the substrate 1 is reflected in the flatness of a metal structure and the flatness of a cell culture plate eventually. Though a technique to form the first resist layer 2 on the substrate 1 is not limited in any way, techniques such as spin coating, dip coating, roll coating, and dry film resist lamination are generally used. Particularly, the spin coating is a technique to deposit a resist on a spinning glass substrate and it has an advantage of very flat coating of a resist on a glass substrate with the diameter of more than 300 mm in diameter. The spin coating is thus preferred for use to achieve high flatness.

There are two types of resists that may be used as the first resist layer 2: positive resist and negative resist. Since the depth of focus on the resist changes depending on the resist sensitivity and exposure conditions, when using a UV exposure system, for example, it is preferred to select an exposure time and a UV output level according to the type, thickness, and sensitivity of the resist. If the resist used is a wet resist, to obtain a given resist thickness by the spin coating, for example, a technique of changing the spin coating rotation speed or a technique of adjusting the viscosity may be used. The technique of changing the spin coating rotation speed obtains a given resist thickness by setting the rotation speed of a spin coater. The method of adjusting the viscosity adjusts the resist viscosity according to the flatness level required for practical use since the degradation of flatness can occur if the resist is thick or the resist deposition area is large.

In the spin coating technique, for example, the thickness of the resist layer deposited at a time is preferably 10 to 50 µm, more preferably 20 to 50 µm, to maintain high flatness. In order to obtain a given resist layer thickness while retaining high flatness, a plurality of resist layers may be formed. When positive resist is used for the first resist layer 2, if a baking time (solvent drying) is too long, the resist hardens too much, making it difficult to form a pattern in the subsequent development step. Thus, it is preferred to select baking conditions by reducing the baking time and so on if the resist thickness is less than 100 µm.

(ii) The positioning of the substrate 1 and a mask 3 is described below. For a given positional relationship between the pattern of the first resist layer 2 and the pattern of the second resist layer 4, accurate positioning is necessary in the exposure using the first mask 3. Positioning techniques include a technique of providing cutting in the corresponding positions of the substrate 1 and the first mask 3 and fixing them with pins, a technique of reading the positions by laser interferometry, and a technique of creating position marks in the corresponding positions of the substrate 1 and the first mask 3 and performing positioning with an optical microscope. The positioning with an optical microscope may create a position mark on the substrate by photolithography and create a position mark on the mask 3 by laser beam equipment, for example. This is effective in that the accuracy within 5 µm can be easily obtained by manual operation using the optical microscope.

(iii) The exposure of the first resist layer 2 with the use of the first mask 3 is described below. The first mask 3 used in the step shown in FIG. 2B is not limited in any way. For example, an emulsion mask, a chrome mask and so on may be used. In the resist pattern formation step, the size and accuracy depend on the mask to be used. The size and accuracy are reflected in the resin molded product. Hence, to obtain a nano/micro structure cell culture plate with a given size and accuracy, it is necessary to specify the size and accuracy of the mask. A technique to increase the accuracy of the mask 3 is not limited in any way. For example, one technique is to change the light that is used for the pattern formation of the mask 3 to the one with a shorter wavelength. This technique, however, requires high facility costs, resulting in higher fabrication costs of the mask. It is thus preferred to specify the mask accuracy according to the accuracy level required for practical use of the nano/micro structure cell culture plate. The material of the mask 3 is preferably quartz glass in terms of temperature expansion coefficient and UV light transmission and absorption characteristics; however, since it is relatively expensive, the material is preferably selected according to the accuracy level required for practical use of the resin molded product. In order to obtain a given structure with different depths or heights or a structure in which the first resist pattern and the second resist pattern are different, it is necessary to ensure the design of the patterns (transmitting/shielding parts) of the masks that are used for the exposure of the first resist layer 2 and the second resist layer 4. One approach to achieve this is to perform simulation by using CAE analysis software.

The light source used for the exposure is preferably a UV lamp or a laser light source for low facility costs. Though synchrotron radiation makes deep exposure, it requires high facility costs and thus substantially increases the price of a nano/micro structure cell culture plate, and therefore it is often not industrially practical. However, use of the synchrotron radiation is effective when a minute pattern of 100 nm or less is required. Since exposure conditions such as exposure time and intensity vary by the material, thickness and so on of the first resist layer 2, they are preferably adjusted according to the pattern to be formed. The adjustment of the exposure conditions is important since it affects the accuracy and the sizes of a pattern such as the width and height of a flow channel, and the interval, width (or diameter) and height of a reservoir. Further, since the depth of focus changes depending on the resist type, when using a UV exposure system, for example, it is preferred to select an exposure time and a UV output level according to the thickness and sensitivity of the resist.

(iv) The heat-treatment on the first resist layer 2 is described below. Annealing is known as a typical heat-treatment after the exposure to correct the shape of the resist pattern. In this case, it aims at chemical crosslinking and is used only when a chemical amplification negative resist is used. The chemical amplification negative resist is mainly composed of two- or three-component system. For example, a terminal epoxy group at an end of a chemical structure is ring-opened by exposure light and crosslinking reaction occurs by the heat-treatment. If the layer thickness is 100 µm, for example, the crosslinking reaction progresses in several minutes by the heat-treatment with the temperature of 100° C. Excessive heat-treatment on the first resist layer 2 makes it difficult to dissolve a non-crosslinked part to form a pattern in the subsequent development step. Thus, if the resist thickness is less than 100 µm, it is preferred to adjust the processing by reducing a heat-treatment time, performing the heat-treatment only on the second resist layer 4 formed later and so on.

Figure 2C:
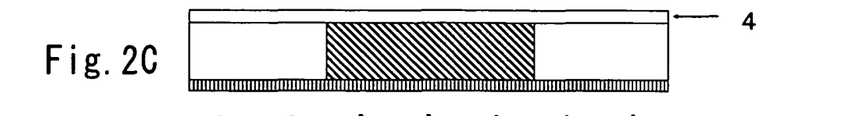

(v) The formation of the second resist layer 4 on the first resist layer 2, which is shown in FIG. 2C, is described below. The forming the second resist layer 4 is performed in the same way as the formation of the first resist layer 2 described in the step (i) except for the following. When forming a resist layer with the use of a positive resist by spin coating, increasing the baking time about 1.5 to 2 times longer than usual allows expressing the alkali resistance. It is thereby possible to prevent the dissolution or distortion of the resist pattern of the second resist layer 4 at the completion of the development of the first resist layer 2 and the second resist layer 4.

Figure 2D:
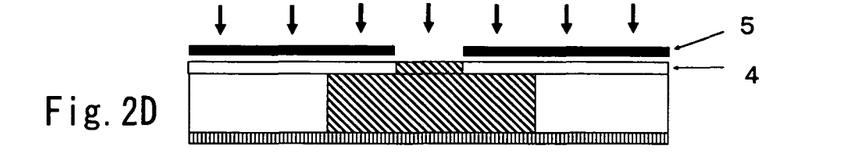

(vi) The positioning of the substrate 1 and the second mask 5 is described below. The positioning is performed in the same manner as the positioning described in the step (ii).

(vii) The exposure of the second resist layer 4 with the use of the second mask 5 is described below. The exposure is performed in the same manner as the exposure described in the step (iii).

(viii) The heat-treatment on the second resist layer 4 is described below. The heat-treatment is basically the same as the heat-treatment described in the step (iv) except for the followings. The heat-treatment on the second resist layer 4 is performed in order to avoid the dissolution or distortion of the pattern of the second resist layer 4 when the pattern of the first resist layer 2 is formed in the subsequent development step. The heat-treatment enhances the chemical crosslinking to increase the crosslink density, thereby expressing the alkali resistance. The heat-treatment time for expressing the alkali resistance is preferably selected from the range of 1.1 to 2.0 times longer than usual according to the resist thickness.

(ix) The development of the resist layers is described below. The development performed in the step shown in FIG. 2E preferably uses a prescribed developer suitable for the resist used. It is further preferred to adjust development conditions such as development time, development temperature and developer density according to the resist thickness and pattern shape. Setting appropriate conditions is preferred since overlong development time causes a removed part to be larger than a predetermined size, for example. As the entire thickness of the resist layers increases, the width (or diameter) of the top surface of the resist may become undesirably larger than that of the bottom of the resist in the development step. Thus, when forming a plurality of resist layers, it is preferred in some cases to form different resist with different sensitivity in each resist layer formation step. In this case, the sensitivity of the resist layer close to the top may be set higher than that of the resist layer close to the bottom. Specifically, BMR C-1000PM manufactured by TOKYO OHKA KOGYO CO., LTD. may be used as the higher sensitivity resist and PMER-N-CA3000PM manufactured by TOKYO OHKA KOGYO CO., LTD. may be used as the lower sensitivity resist. It is also possible to adjust the sensitivity by changing the drying time of the resists. For example, in the case of using BMR C-1000PM manufactured by TOKYO OHKA KOGYO CO., LTD., drying of the first resist layer for 40 minutes at 110° C. and the second resist layer for 20 minutes at 110° C. in a resist drying step after the spin coating allow the first resist layer to have the higher sensitivity.

Techniques for increasing the flatness accuracy of the top surface of a molded product or the bottom of a minute pattern involve a technique of changing the type of resist (negative or positive) used in the resist coating and a technique of polishing the surface of a metal structure, for example. When forming a plurality of resist layers to obtain a given pattern depth, the process may perform the exposure and development on the plurality of resist layers at the same time, or may form and expose one resist layer and further form and expose another resist layer and then perform the development on the two resist layers at the same time just like this embodiment.

The metal structure formation step is described in further detail with reference to FIGS. 2F and 2G. The metal structure formation step deposits a metal over the resist pattern formed by the resist pattern formation step to form an uneven surface of a metal structure in accordance with the resist pattern, thereby obtaining the metal structure. This step first deposits a conductive layer 7 in accordance with the resist pattern as shown in FIG. 2F. Though a technique of forming the conductive layer 7 is not particularly limited, it is preferred to use vapor deposition, sputtering and so on. A conductive material used for the conductive layer 7 may be gold, silver, platinum, copper, and aluminum, nickel and so on, for example. After forming the conductive layer 7, a metal is deposited in accordance with the pattern by plating, thereby forming the metal structure 8 as shown in FIG. 2G. A plating technique for depositing the metal is not particularly limited, and electroplating or electroless plating may be used, for example. A metal used is also not particularly limited, and nickel, nickel and cobalt alloy, copper, or gold may be used, for example. Nickel is preferred since it is durable and less costly. The metal structure 8 deposited by plating is then separated from the resist pattern.

The metal structure 8 may be polished depending on its surface condition. In this case, to prevent contaminations from attaching to a product, it is preferred to perform ultrasonic cleaning after the polishing. Further, it is also possible to perform surface treatment of the metal structure 8 by using mold release agent or the like so as to improve the surface condition. The angle of gradient along the depth direction of the metal structure 8 is preferably 50° to 90°, and more preferably, 60° to 87°. The polishing may be performed before or after separating the metal structure 8 from the resist pattern.

The molded product formation step is described hereinafter in further detail. The molded product formation step uses the metal structure 8 as a mold to form a resin molded product 9 as shown in FIG. 2H. Though a technique for forming the resin molded product 9 is not particularly limited, injection molding, press molding, monomer casting, solution casting, roll transfer by extrusion molding and so on may be used, for example. The injection molding is preferred for its high productivity and pattern reproducibility. If the resin molded product 9 is formed by the injection molding by using the metal structure 8 with a prescribed size as a mold, it is able to reproduce the shape of the metal structure 8 into the resin molded product 9 with a high reproduction rate. The reproduction rate may be checked by using an optical microscope, a scanning electron microscope (SEM), a transmission electron microscope (TEM) and so on.

In the case of producing the resin molded product 9 with the use of the metal structure 8 as a mold by the injection molding, for example, 10,000 to 50,000 pieces or even 200,000 pieces of resin molded products may be obtained with one metal structure 8. It is thereby possible to largely eliminate the costs for producing the metal structures 8. Besides, one cycle of injection molding takes only 5 to 30 seconds, being highly productive. The productivity further increases with the use of a mold capable of simultaneous production of a plurality of resin molded products in one injection molding cycle. In this molding process, the metal structure 8 may be used as a metal mold; alternatively, the metal structure 8 may be placed inside a prepared metal mold.

A resin material used for the formation of the resin molded product 9 is not particularly limited. Acrylic resin, polylactide resin, polyglycolic acid resin, styrene resin, acrylic-styrene copolymer (MS resin), polycarbonate resin, polyester resin such as polyethylene terephthalate, polyvinyl alcohol resin, ethylene-vinyl alcohol copolymer, thermoplastic elastomer such as styrene elastomer, vinyl chloride resin, or silicone resin such as polydimethylsiloxane may be used, for example. The above resin may contain one or more than one agent of lubricant, light stabilizer, heat stabilizer, antifogging agent, pigment, flame retardant, antistatic agent, mold release agent, antiblocking agent, ultraviolet absorbent, antioxidant and so on.

The minimum value of the flatness of the resin molded product 9 is preferably 1 μm or larger in order to enable easy industrial reproduction. The maximum value of the flatness of the resin molded product 9 is preferably 200 μm or smaller in order not to cause any problem in the attachment or lamination of the molded product 9 with another substrate. The dimensional accuracy of the pattern of the resin molded product 9 is preferably within the range of ±0.5% to 10% in order to enable easy industrial reproduction. The dimensional accuracy of the thickness of the resin molded product 9 is also preferably within the range of ±0.5% to 10% in order to enable easy industrial reproduction. Though the thickness of the resin molded product 9 is not particularly specified, it is preferably within the range of 0.2 to 10 mm in order to prevent breakage at removal in the injection molding, or breakage, deformation or distortion during processing. The size of the resin molded product 9 is also not particularly specified, and it is preferably selected according to usage. For example, when forming the resist pattern by lithography technique, if the resist layer is formed by spin coating, the diameter is preferably within 400 mm.

EXAMPLES

Preferred examples of a culture plate and a method of producing the culture plate are described hereinbelow. Though the present invention is described in detail in conjunction with several examples, it is not limited to these examples.

Referring first to FIG. 2A, the first resist coating on a substrate was performed by using an organic material (PMER N-CA3000PM manufactured by TOKYO OHKA KOGYO CO., LTD.). Referring next to FIG. 2B, after the first resist layer formation, positioning of the substrate and a first mask that had been processed to have a given mask pattern was performed.

After that, the first resist layer was exposed to UV light by a UV exposure system (PLA-501F manufactured by CANON INC. with the wavelength of 365 nm and the exposure dose of 300 mJ/cm$^2$). The first resist layer was then heat-treated using a hot plate at 100° C. for 4 minutes. Referring then to FIG. 2C, the second resist coating on the substrate was performed by using an organic material (PMER N-CA3000P manufactured by TOKYO OHKA KOGYO CO., LTD.). Referring further to FIG. 2D, after the second resist layer formation, positioning of the substrate and a second mask with a given mask pattern was performed. After that, the second resist layer was exposed to UV light by a UV exposure system (PLA-501F manufactured by CANON INC. with the wavelength of 365 nm and the exposure dose of 100 mJ/cm$^2$). The second resist layer was then heat-treated by using a hot plate at 100° C. for 8 minutes.

Figure 2E:
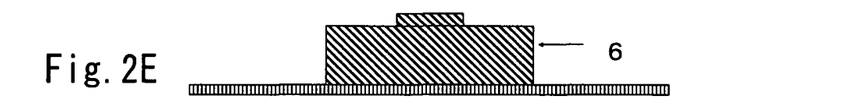
Figure 2F:
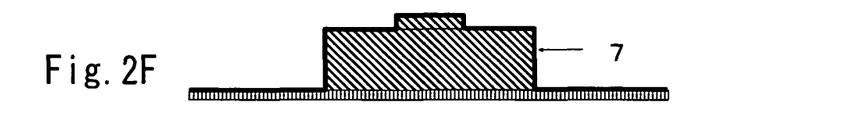
Figure 2G:
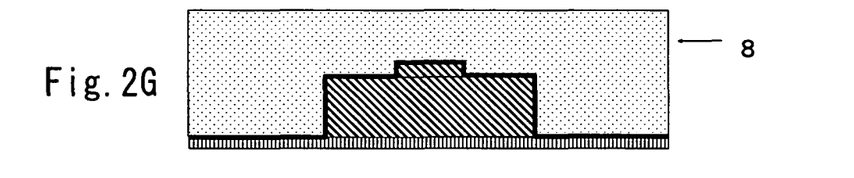
Figure 2H:
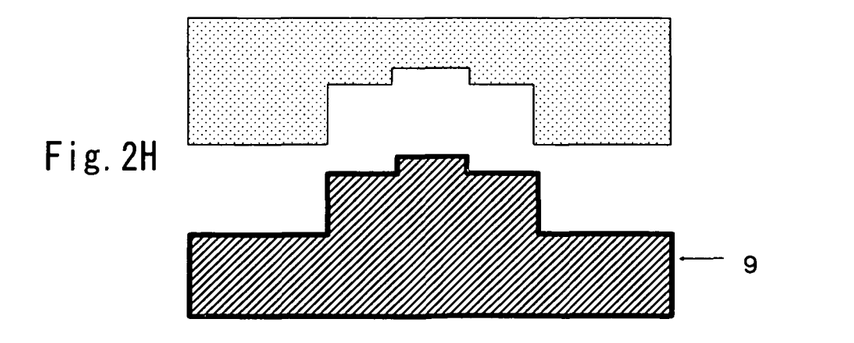

Referring then to FIG. 2E, development was performed on the substrate having the resist layers, thereby forming a resist pattern on the substrate (developer: PMER developer P-7G manufactured by TOKYO OHKA KOGYO CO., LTD.). Further, referring to FIG. 2F, vapor deposition was performed on the surface of the substrate with the resist pattern, thereby depositing a conductive layer formed of silver on the surface of the resist pattern. Referring then to FIG. 2G, the substrate having the resist pattern was soaked in nickel plating solution for electroplating, thereby creating a metal structure (hereinafter referred to as the nickel structure) onto which the resist pattern was inscribed. Referring finally to FIG. 2H, the nickel structure was attached to the mold and the pattern of the nickel structure was inscribed, thereby producing a plastic molded product.

<Cell Culture Plate 1>

Figure 3A:
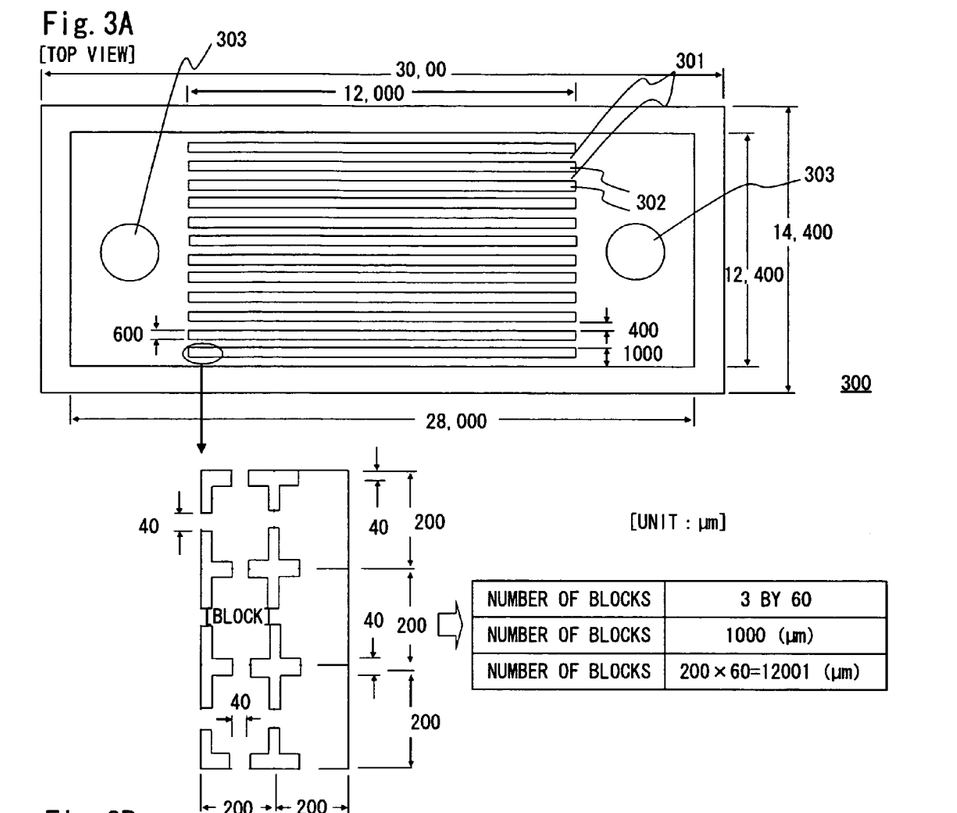
FIGS. 3A and 3B are block diagrams showing the structure of a cell culture plate according to an embodiment of the present invention.
Figure 3B:
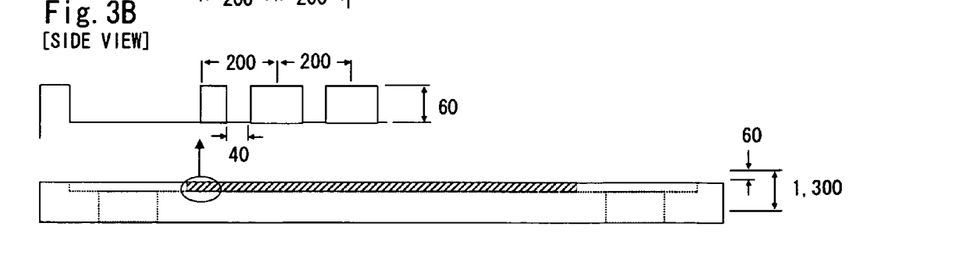

According to the molded product production process shown in FIGS. 2A to 2H, the resist coating was repeated twice to form the first resist layer and then exposure and heat-treatment were performed on each layer. Further, the resist coating was performed once again to form the second resist layer, and then the exposure and the heat-treatment were performed thereon. A cell culture plate 300 as shown in FIGS. 3A and 3B is thereby produced. The cell culture plate 300 has a substrate with 30 mm in width, 14.4 mm in length and 1.3 mm in thickness, on which a plurality of flow channels 301, uneven pattern areas 302 and through holes 303 are formed. In FIGS. 3A and 3B, only some of flow channels and uneven pattern areas are denoted by reference numerals. The flow channels 301 are formed between the uneven pattern areas 302 so that culture solution flows from the flow channels 301 into the uneven pattern areas 302 or from the uneven pattern areas 302 into the flow channels 301.

In the uneven pattern areas 302, a cell culture space and a flow channel are created by the uneven patterns. A plurality of protrusions that are arranged regularly are formed in the uneven pattern areas 302 so that culture solution flows through a gap between the protrusions. The culture solution inflowing through one through hole 303 flows through the flow channel 301 and the uneven pattern area 302 to be discharged through the other through hole 303. It is thereby possible to supply new culture solution and discharge by-products. Each flow channel 301 has a width of 400 μm, a length of 12,000 μm and a depth of 60 μm. The uneven pattern area 302 has a width of 600 μm and a length of 12,000 μm. The uneven pattern area 302 has an opening (gap between protrusions) with a size of 40 μm and a rectangular spatial structure with a height of 60 μm, a width of 160 μm and a depth of 160 μm. A pitch between protrusions is 200 μm.

<Cell Culture Plate 2>

Figure 4A:
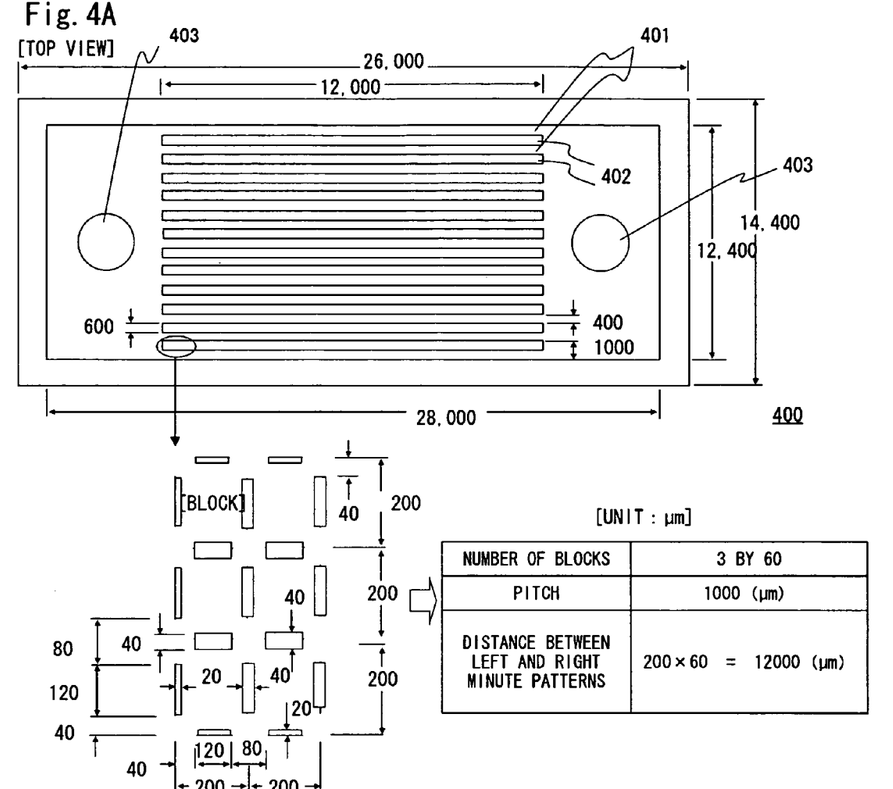
FIGS. 4A and 4B are block diagrams showing the structure of a cell culture plate according to an embodiment of the present invention.
Figure 4B:
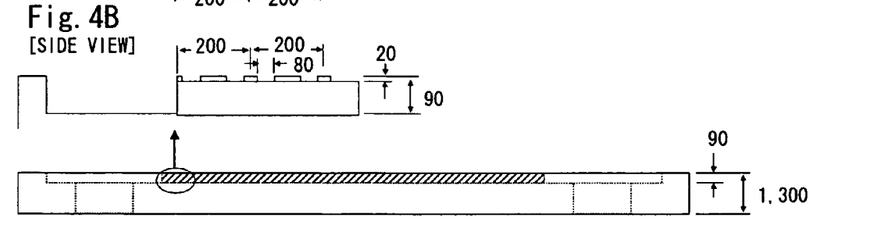

According to the molded product production process shown in FIGS. 2A to 2H, the resist coating was repeated twice to form the first resist layer and then exposure and heat-treatment were performed on each layer. Further, the resist coating was performed once again to form the second resist layer, and then the exposure and the heat-treatment were performed thereon. A cell culture plate 400 as shown in FIGS. 4A and 4B is thereby produced. The cell culture plate 400 has a substrate with 30 mm in width, 14.4 mm in length and 1.3 mm in thickness, on which a plurality of flow channels 401, uneven pattern areas 402 and through holes 403 are formed. In FIGS. 4A and 4B, only some of flow channels and uneven pattern areas are denoted by reference numerals. Each flow channel 401 has a width of 400 μm, a length of 12,000 μm and a depth of 70 μm. In the uneven pattern areas 402, a cell culture space (block) and a flow channel are created by the uneven patterns. A plurality of protrusions are formed in the uneven pattern areas 402 so that culture solution flows through a gap between the protrusions. The uneven pattern area 402 has a width of 600 μm and a length of 12,000 μm. Further, the uneven pattern area 402 has an opening with a size of 80 μm and an even pattern with a height of 20 μm. A pitch between protrusions in the longitudinal direction of the uneven pattern areas 402 is 200 μm. The uneven pattern area 402 further has a rectangular spatial structure with a height of 20 μm, a width of 160 μm and a depth of 160 μm.

<Cell Culture Plate 3>

Figure 5A:
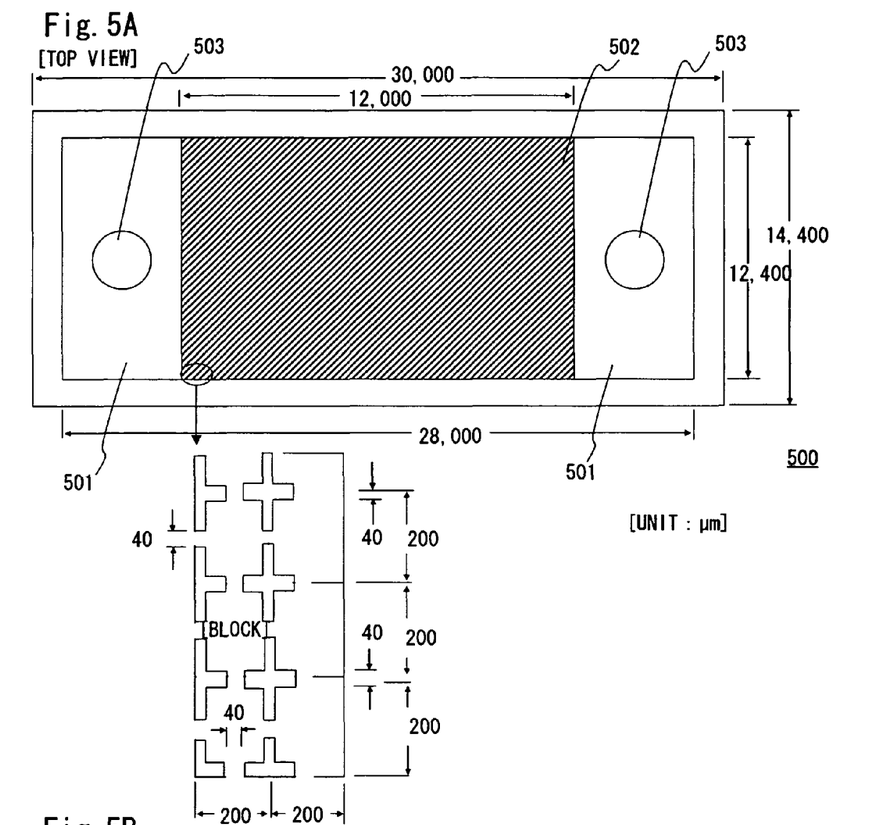
FIGS. 5A and 5B are block diagrams showing the structure of a cell culture plate according to an embodiment of the present invention.
Figure 5B:
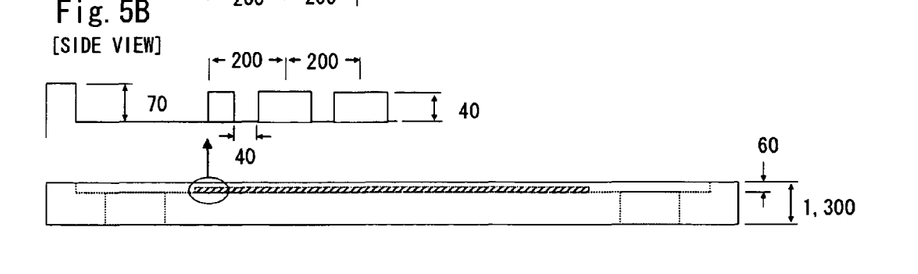

According to the molded product production process shown in FIGS. 2A to 2H, the resist coating was repeated twice to form the first resist layer and then exposure and heat-treatment were performed on each layer. Further, the resist coating was performed once again to form the second resist layer, and then the exposure and the heat-treatment were performed thereon. A cell culture plate 500 as shown in FIGS. 5A and 5B is thereby produced. The cell culture plate 500 has a substrate with 30 mm in width, 14.4 mm in length and 1.3 mm in thickness, on which a flow channel 501, an uneven pattern area 502 and a plurality of through holes 503 for circulating culture solution are formed. The flow channel 501 has a width of 12,400 μm and a depth of 70 μm. The uneven pattern area 502 has an opening with a size of 40 μm and an uneven pattern with a height of 40 μm. The pattern shape in the uneven pattern area 502 is substantially the same as the structure shown in FIGS. 3A and 3B.

<Cell Culture Plate 4>

Figure 6A:
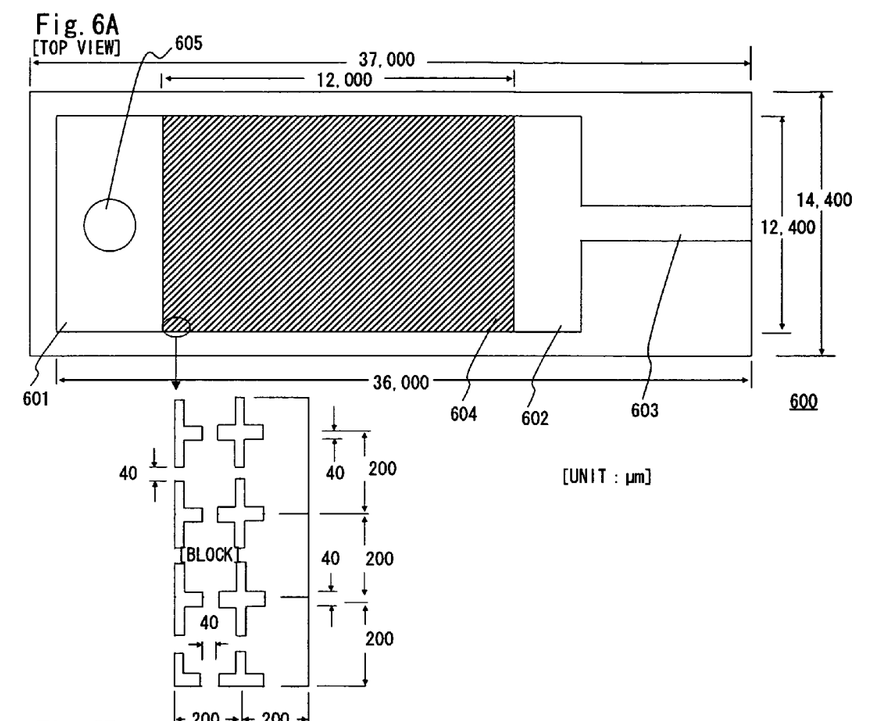
FIGS. 6A and 6B are block diagrams showing the structure of a cell culture plate according to an embodiment of the present invention.
Figure 6B:
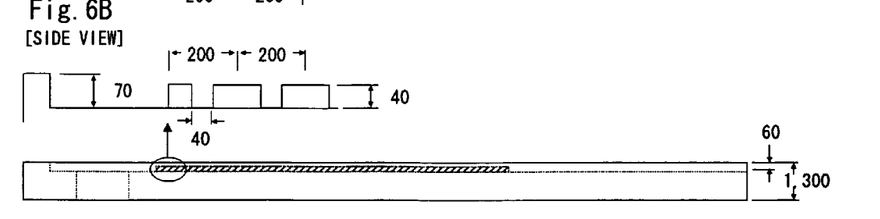

According to the molded product production process shown in FIGS. 2A to 2H, the resist coating was repeated twice to form the first resist layer and then exposure and heat-treatment were performed on each layer. Further, the resist coating was performed once again to form the second resist layer, and then the exposure and the heat-treatment were performed thereon. A cell culture plate 600 as shown in FIGS. 6A and 6B is thereby produced. The cell culture plate 600 has a substrate with 37 mm in width, 14.4 mm in length and 1.3 mm in thickness, on which flow channels 601 to 603, an uneven pattern area 604 and a through hole 605 for circulating culture solution are formed. The flow channels 601 and 602 have a width of 12,400 μm and a depth of 70 μm. The uneven pattern area 604 has an opening with a size of 40 μm and an uneven pattern with a height of 40 μm. The pattern shape in the uneven pattern area 604 is substantially the same as the structure shown in FIGS. 3A and 3B.

[Preparation of Cell Culture Plates 1 to 4]

The cell culture plates 1 to 4 formed of acryl were used. Ultrasonic cleaning with ethanol and pure water was performed thereon and the plates were dried sufficiently. Then, collagen for enhancing cell adhesion was applied thereto, thereby producing plates for culturing cells.

[Conditioning of Comparative Culture Plates A and B]

A culture plate A having 24-well plate formed of polystyrene and a culture plate B having 1536-well plate formed of polystyrene were used. Gamma sterilization was performed thereon. Then, collagen for enhancing cell adhesion was applied thereto, thereby producing a plate for culturing cells.

[Cell Culture Environment on Culture Plate]

Rat bone marrow stromal cells and chicken embryo fibroblast cells that had been isolated from a rat bone marrow and a chicken embryo heart and cultured were placed on the uneven pattern areas of the cell culture plates 1 to 4 and on the wells of the comparative culture plates A and B. The cell culture plates were soaked in culture solution and overlapped with an acrylic plate so as to circulate the culture solution by through holes. The comparative culture plates were soaked in culture solution in a dish, and the comparison of the culture environments most suitable for cell differentiation and cell growth were made.

[Comparison of Cell Culture on Culture Plate]

Three days of cell culture test showed that the cell culture plates were able to supply constantly fresh culture solution, and therefore the culture solution was not replaced. On the other hand, the culture solution in the comparative cell culture plates A and B was replaced on the second day. Since the cells were cultured on a flat plate in the comparative culture plate A, the cells were thinned into a form in lack of direction and inferred to no longer have the features they had had in vivo. Though the comparative culture plate B had been expected to have the effects of culturing cells in a minute uneven pattern since it has a small well plate size, the cells were thinned into a shape without direction. This was probably because in the culturing of the chicken embryo fibroblast cells, for example, which are difficult to culture, the PH of culture solution changed due to waste products expelled from the cells, affecting the living environment of the cells.

Figure 7:
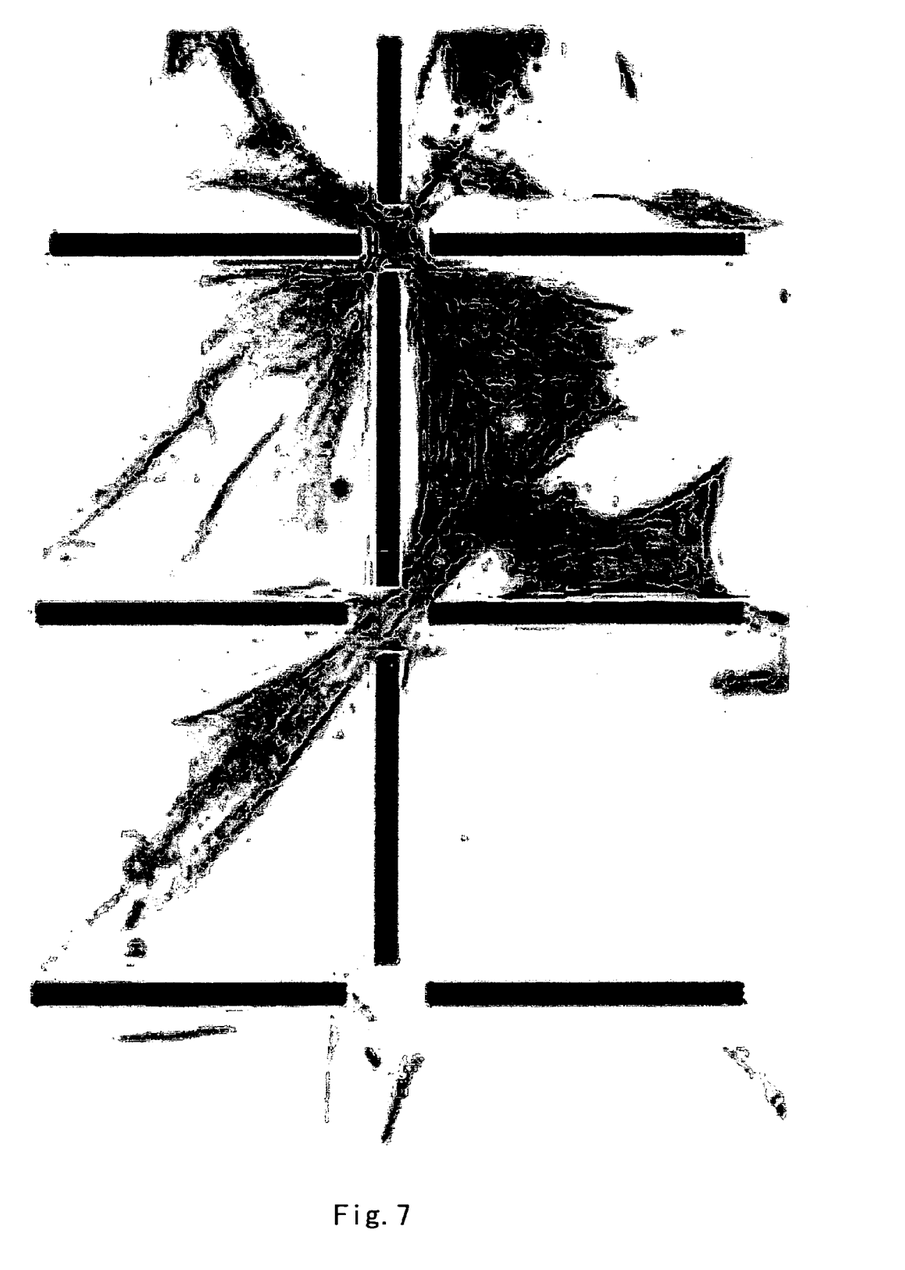
FIG. 7 is a picture showing the result of cell growth with the use of a cell culture plate according to an embodiment of the present invention.

On the other hand, the cell culture plates 1 to 4 achieved culturing the cells in directional forms. It was observed that the rat bone marrow stromal cells grew sterically within the uneven pattern area. It was also observed that the chicken embryo fibroblast cells grew sterically along the walls of the uneven pattern. It was thus proved that the bone marrow stromal cells and the embryo fibroblast cells grew in different manner. FIG. 7 is a picture showing the result of the cell growth in Example 2 which was observed by using a fluorescence biomicroscope (type: VB) manufactured by KEYENCE CORPORATION. It indicates that the cells form tissues by differentiation and growth. In FIG. 7, the walls of the uneven pattern arranged lattice-like were added to the picture showing the cell growth result afterward by composite for the purpose of clarifying the shown objects. Further, in this example, the width of the wall of the uneven pattern (the shorter side of the wall in FIG. 7) was approximately 40 μm, and the width of one space defined by the walls was approximately 160 μm. On the other hand, it was unable to obtain such a picture with the comparative cell culture plates A and B, which means that the cells were not able to form tissues. This result indicates that it is possible to culture the cells whose growth has been difficult in a steric space by removing waste products. Thus, the culture plate of the present invention is effective for use as a culture plate to enable researches of differentiation, grows, wandering and so on of various types of cells.

The cell culture plate of this embodiment enables the growth of the cells that have been difficult to culture, and it is possible to provide a culture plate that is suitable for bioassay or the like of drugs by maintaining the features observed in vivo. Specifically, the flow channels for supplying culture solution to cells allow the supply of fresh culture solution to a cell medium and also allow the removal of waste products expelled from the cells. The culture plate can thereby express the features observed in vivo.

It is apparent that the present invention is not limited to the above embodiment that may be modified and changed without departing from the scope and spirit of the invention.

What is claimed is:

1. A cell culture plate, comprising:
   a bottom surface having an uneven pattern area and flow channel(s) separate from the uneven pattern, wherein the uneven pattern area comprises a pattern of discontinuous walls defining rectangular spatial compartments for culturing cells and where said walls are substantially perpendicular to the bottom surface of the plate and have a height ranging from 3 to 1,000 μm, a width ranging from 3 to 500 μm, and a depth ranging from 3 to 500 μm;

wherein the flow channel(s) are interconnected with the uneven pattern area so that they can supply the rectangular spatial compartments for culturing cells with fresh culture solution and/or receive waste products from cells cultured in the rectangular spatial compartments;

wherein said cell culture plate is formed from thermoplastic resin in an integrated manner, where said thermoplastic resin is one or more than one material selected from the group consisting of acrylic resin, polylactide resin, polyglycolic acid resin, styrene resin, acrylic-styrene copolymer (MS resin), polycarbonate resin, polyester resin, polyvinyl alcohol resin, ethylene-vinyl alcohol copolymer, thermoplastic elastomer, vinyl chloride resin, silicone resin, and combinations thereof; and wherein a surface of the cell culture plate for culturing cells has been treated to immobilize cells.

2. The cell culture plate according to claim 1, wherein said surface of the cell culture plate has been treated with at least one of low temperature plasma, corona discharge or ultraviolet radiation in a manner that enhances the adhesion of cells cultivated in the cell culture plate to the surface of the cell culture plate.

3. The cell culture plate according to claim 1, wherein the cell culture plate is a resin molded product.

4. The cell culture plate according to claim 1, wherein the cell culture plate is a lamination of a plurality of plates.

5. The cell culture plate according to claim 1, further comprising cultured cells.

6. The cell culture plate of claim 1, further comprising cultured cells which retain characteristics they have in vivo, which characteristics are absent from cells cultured in an otherwise similar cell culture plate not having the uneven pattern area comprising a pattern of discontinuous walls defining rectangular spatial compartments.

7. The cell culture plate of claim 1, wherein the discontinuous walls defining rectangular spatial compartments have a depth and/or width ranging from 5 μm to 160 μm.

8. The cell culture plate of claim 1, wherein the height of the discontinuous walls defining rectangular spatial compartments ranges from 3 μm to 500 μm.

9. The cell culture plate of claim 1, wherein the height of the discontinuous walls defining rectangular spatial compartments ranges from 5 μm to 300 μm.

10. The cell culture plate of claim 1, wherein the discontinuous walls defining rectangular spatial compartments when viewed from above are cross-shaped, T-shaped, L-shaped, or I-shaped.

11. The cell culture plate of claim 1, wherein the
the bottom surface of each spatial compartment is interconnected through its corners with those of adjacent spatial compartments; or the bottom surface of each spatial compartment is interconnected through its sides with those of adjacent spatial compartments.

12. The cell culture plate of claim 1 that has a bottom that retains liquids.

13. The cell culture plate of claim 1, wherein said surface of the cell culture plate has been treated with at least one of collagen or another protein in a manner that enhances the adhesion of cells cultivated in the cell culture plate to the surface of the cell culture plate.

14. The cell culture plate of claim 1 in which rat bone marrow stromal cells or chicken embryo fibroblast cells grow directionally or in which cultures rat bone marrow stromal cells or chicken embryo fibroblast cells grow sterically.

15. The cell culture plate of claim 1, further comprising a mixing portion where culture solution and/or reagent are mixed.

16. The cell culture plate of claim 1, further comprising an electrode for electrical cell fusion.

17. The cell culture plate according to claim 1, wherein a width of the flow channel of the cell culture plate is from 1 to 1,000 μm and a depth of the flow channel is from 1 μm to 1,000 μm.

* * * * *